US011302171B2

(12) United States Patent
Colunga et al.

(10) Patent No.: US 11,302,171 B2
(45) Date of Patent: Apr. 12, 2022

(54) SWIMMER SAFETY MONITOR APPARATUS

(71) Applicants: Orlando Colunga, George West, TX (US); Ana Torres, George West, TX (US)

(72) Inventors: Orlando Colunga, George West, TX (US); Ana Torres, George West, TX (US)

( * ) Notice: Subject to any disclaimer, the term of this patent is extended or adjusted under 35 U.S.C. 154(b) by 6 days.

(21) Appl. No.: 16/904,265

(22) Filed: Jun. 17, 2020

(65) Prior Publication Data

US 2021/0398413 A1 Dec. 23, 2021

(51) Int. Cl.
| G08B 21/08 | (2006.01) |
| G08B 21/02 | (2006.01) |
| A61B 5/00 | (2006.01) |
| A61B 5/11 | (2006.01) |
| A61B 5/0205 | (2006.01) |
| G08B 21/04 | (2006.01) |
| A61B 5/08 | (2006.01) |
| A61B 5/024 | (2006.01) |
| A61B 5/021 | (2006.01) |

(52) U.S. Cl.
CPC ............ *G08B 21/088* (2013.01); *A61B 5/002* (2013.01); *A61B 5/02055* (2013.01); *A61B 5/1112* (2013.01); *A61B 5/681* (2013.01); *A61B 5/6831* (2013.01); *A61B 5/746* (2013.01); *A61B 5/747* (2013.01); *G08B 21/0269* (2013.01); *G08B 21/0288* (2013.01); *G08B 21/0453* (2013.01); *A61B 5/021* (2013.01); *A61B 5/024* (2013.01); *A61B 5/0816* (2013.01); *A61B 2503/06* (2013.01); *A61B 2503/10* (2013.01); *A61B 2560/0214* (2013.01)

(58) Field of Classification Search
CPC .............. G08B 21/088; G08B 21/0453; G08B 21/0269; G08B 21/0288; A61B 5/681; A61B 5/747; A61B 5/6831; A61B 5/1112; A61B 5/746; A61B 5/02055; A61B 5/002; A61B 5/021; A61B 2560/0214; A61B 2503/10; A61B 5/024; A61B 2503/06; A61B 5/0816
USPC .................................................... 340/539.12
See application file for complete search history.

(56) References Cited

U.S. PATENT DOCUMENTS

| 7,479,891 | B2 | 1/2009 | Boujon | |
| 8,107,920 | B2 * | 1/2012 | Ben Ayed | A61B 5/002 |
| | | | | 455/404.1 |
| 8,647,268 | B2 * | 2/2014 | Tran | A61B 5/1117 |
| | | | | 600/301 |

(Continued)

FOREIGN PATENT DOCUMENTS

WO    WO2004015644    2/2004

*Primary Examiner* — Omar Casillashernandez

(57) ABSTRACT

A swimmer safety monitor apparatus for allowing adults to monitor swimming children's safety to prevent drowning includes a transmitter body and a strap coupled to the transmitter body to secure the apparatus on a user's wrist. A transmitter display is coupled to a body front side of the transmitter body. A CPU is coupled within the transmitter body and is in operational communication with the transmitter display. A battery, a biometric sensor, a power button, a panic button, and a transceiver are coupled to the transmitter body and are in operational communication with the CPU to communicate with a personal electronic device to send vitals from the biometric sensor and alerts from the panic button.

12 Claims, 4 Drawing Sheets

(56) References Cited

U.S. PATENT DOCUMENTS

| | | | |
|---|---|---|---|
| 9,069,333 B1* | 6/2015 | Romans | G04G 21/025 |
| 9,892,609 B2* | 2/2018 | Kim | G08B 21/0453 |
| 10,105,108 B1* | 10/2018 | Taptelis | G16H 80/00 |
| 10,123,702 B1* | 11/2018 | Wilkins | A61B 5/747 |
| 10,298,339 B2 | 5/2019 | Snyder | |
| 10,542,628 B2* | 1/2020 | Prest | H05K 5/0017 |
| 11,062,584 B1* | 7/2021 | Magaletta | G04G 21/04 |
| 2003/0173408 A1* | 9/2003 | Mosher, Jr. | A61B 90/90 |
| | | | 235/492 |
| 2005/0250440 A1* | 11/2005 | Zhou | G01S 19/17 |
| | | | 455/12.1 |
| 2008/0266118 A1* | 10/2008 | Pierson | A61B 5/6826 |
| | | | 340/573.6 |
| 2010/0032462 A1* | 2/2010 | Cameron | A45F 5/00 |
| | | | 224/222 |
| 2012/0022382 A1* | 1/2012 | Daisuke | A61B 5/14551 |
| | | | 600/481 |
| 2015/0287338 A1* | 10/2015 | Wells | G09B 23/288 |
| | | | 702/19 |
| 2015/0334530 A1* | 11/2015 | Scott | G08B 25/016 |
| | | | 455/456.1 |
| 2017/0188945 A1 | 7/2017 | Lin | |
| 2018/0357887 A1* | 12/2018 | Geyer | G08B 25/016 |
| 2019/0228633 A1* | 7/2019 | Tobiassen | G08B 21/0446 |
| 2020/0214613 A1* | 7/2020 | O'Connell | A61B 5/0205 |
| 2020/0320851 A1* | 10/2020 | Deutsch | G08B 21/0446 |

\* cited by examiner

SWIMMER SAFETY MONITOR APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

) STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to swimmer safety devices and more particularly pertains to a new swimmer safety device for allowing adults to monitor swimming children's safety to prevent drowning.

(2) Description of Related Art Including Information Disclosed Under 37 CFR 1.97 and 1.98

The prior art relates to swimmer safety devices. Existing devices may monitor vital signs and send panic signals but lack GPS location sharing. Existing devices also fail to incorporate with a monitoring system that allows for many transmitter devices to be simultaneously observed.

) BRIEF SUMMARY OF THE INVENTION

An embodiment of the disclosure meets the needs presented above by generally comprising a transmitter body having a body front side, a body back side, a body top side, a body bottom side, a body left side, and a body right side. A strap is coupled to the transmitter body. The strap includes a first half coupled to the body bottom side and a second half coupled to the body top side. The first half and the second half are selectively engageable to secure the strap and the transmitter body on a user's wrist. A transmitter display is coupled to the body front side of the transmitter body. A CPU is coupled within the transmitter body and is in operational communication with the transmitter display. A battery, a power button, and a panic button are coupled to the transmitter body and are in operational communication with the CPU. A biometric sensor is coupled to the body back side and is in operational communication with the CPU. A transceiver is coupled within the transmitter body and is in operational communication with the CPU. The transceiver is configured to communicate with a personal electronic device to send vitals from the biometric sensor and alerts from the panic button.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

(j) DETAILED DESCRIPTION OF THE INVENTION

Figure 1:
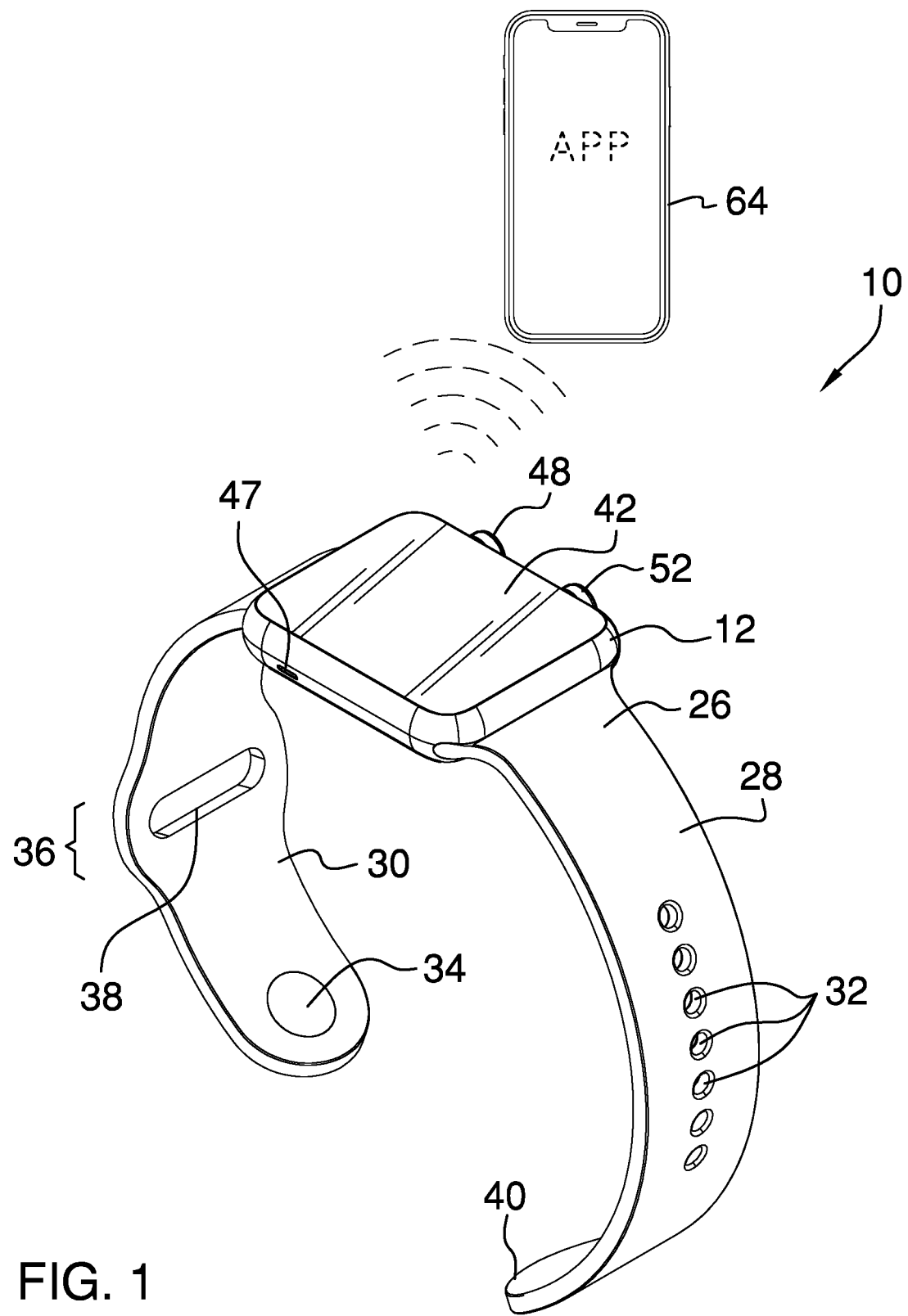
FIG. 1 is an isometric view of a swimmer safety monitor apparatus according to an embodiment of the disclosure.
Figure 2:
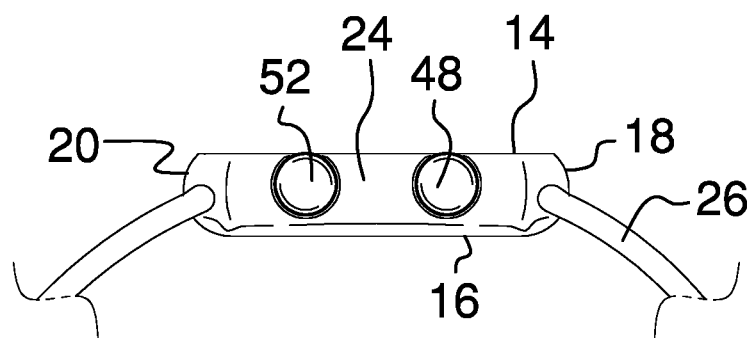
FIG. 2 is a side elevation view of an embodiment of the disclosure.
Figure 3:
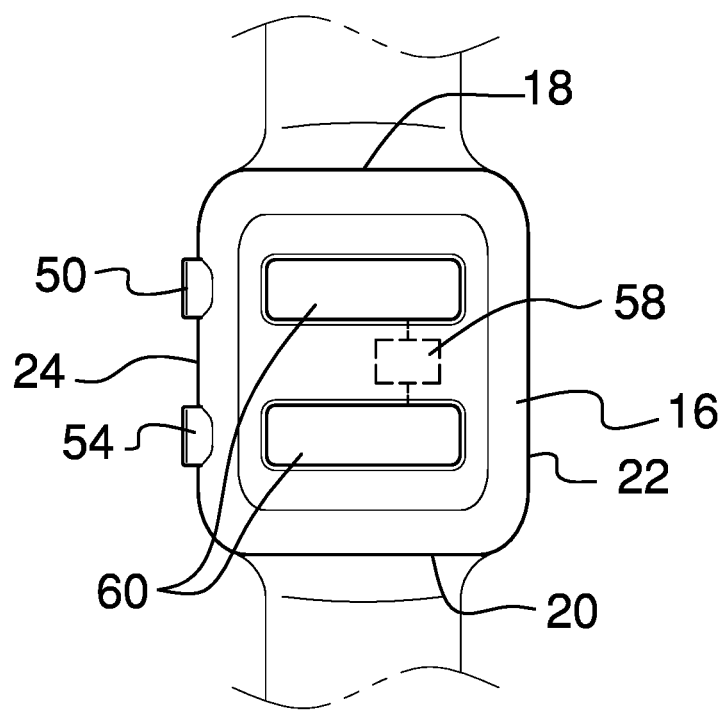
FIG. 3 is a back plan view of an embodiment of the disclosure.
Figure 4:
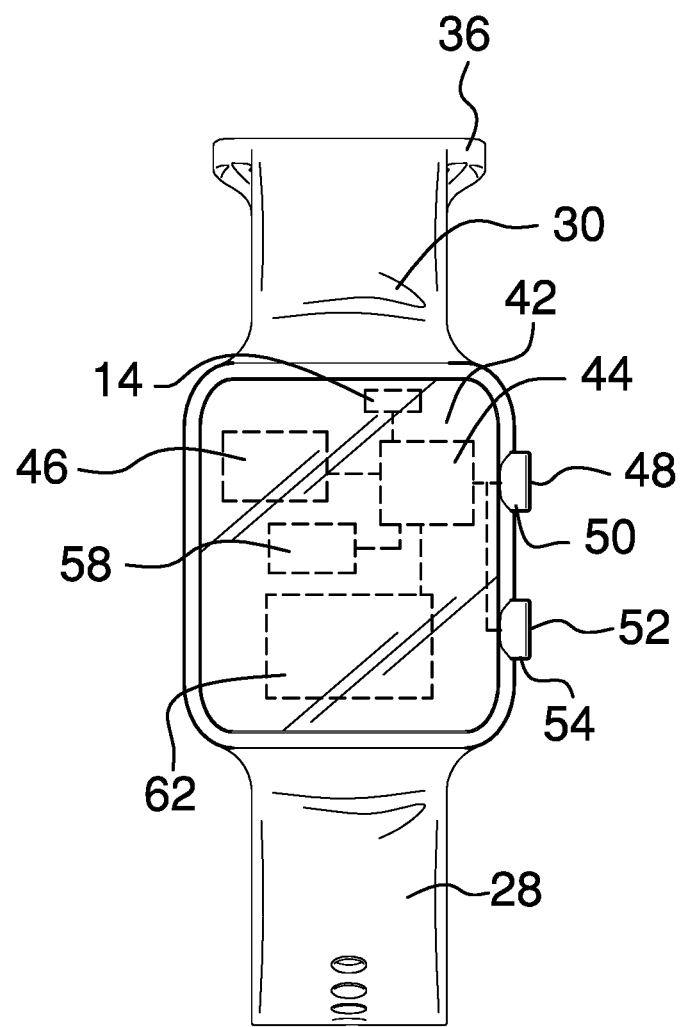
FIG. 4 is a front plan view of an embodiment of the disclosure.

With reference now to the drawings, and in particular to FIGS. 1 through 5 thereof, a new swimmer safety device embodying the principles and concepts of an embodiment of the disclosure and generally designated by the reference numeral 10 will be described.

As best illustrated in FIGS. 1 through 5, the swimmer safety monitor apparatus 10 generally comprises a transmitter body 12 having a body front side 14, a body back side 16, a body top side 18, a body bottom side 20, a body left side 22, and a body right side 24. The body top side 18, the body bottom side 20, the body left side 22, and the body right side 24 may be rounded for improved user comfort.

A strap 26 is coupled to the transmitter body 12. The strap 26 includes a first half 28 coupled to the body bottom side 20 and a second half 30 coupled to the body top side 18. The first half 28 and the second half 30 are selectively engageable to secure the strap 26 and the transmitter body 12 on a user's wrist. The first half 28 of the strap may have a plurality of adjustment apertures 32 and the second half 30 of the strap may have a buckle 34 to selectively engage with the plurality of adjustment apertures 32. The second half 30 of the strap may have a flared portion 36 and an obround strap aperture 38 extending therethrough. The strap aperture 38 receives a distal end 40 of the first half of the strap to secure the strap 26 from moving.

A transmitter display 42 is coupled to the transmitter body 12. The transmitter display 42 may occupy the entirety of the body front side 14. A CPU 44 is coupled within the transmitter body 12 and is in operational communication with the transmitter display 42. A battery 46 is coupled within the transmitter body 12 and is in operational communication with the CPU 44. The battery 46 may have a charge port 47 extending through the body left side 22. The battery 46 may alternatively be chargeable using an inductive charger.

A power button 48 is coupled to the transmitter body 12. The power button 48 is in operational communication with the CPU 44. The power button 48 may have a cylindrical power button housing 50 coupled to the body right side 24 to prevent accidental activation. A panic button 48 is also coupled to the transmitter body 12 and is in operational communication with the CPU 44. The panic button 52 may have a cylindrical panic button housing 54 coupled to the body right side 24 to prevent accidental activation.

A GPS chip 56 may be coupled within the transmitter body 12 is in operational communication with the CPU 44 to identify an exact location of the apparatus 10. A biometric sensor 58 is coupled to the transmitter body 12. The biometric sensor 58 is coupled to the body back side 16 and is in operational communication with the CPU 44. The biometric sensor 58 may comprise a pair of rectangular sensor pads 60 to read the wearer's respiration rate, heart rate, body temperature, and blood pressure.

A transceiver 62 is coupled within the transmitter body 12 and is in operational communication with the CPU 44. The transceiver 62 is configured to communicate with a personal electronic device 64 to send vitals from the biometric sensor 58 and alerts from the panic button 48. An app on the personal electronic device 64 can monitor the location and vitals sent from numerous wearers of the apparatus 10.

Figure 5:
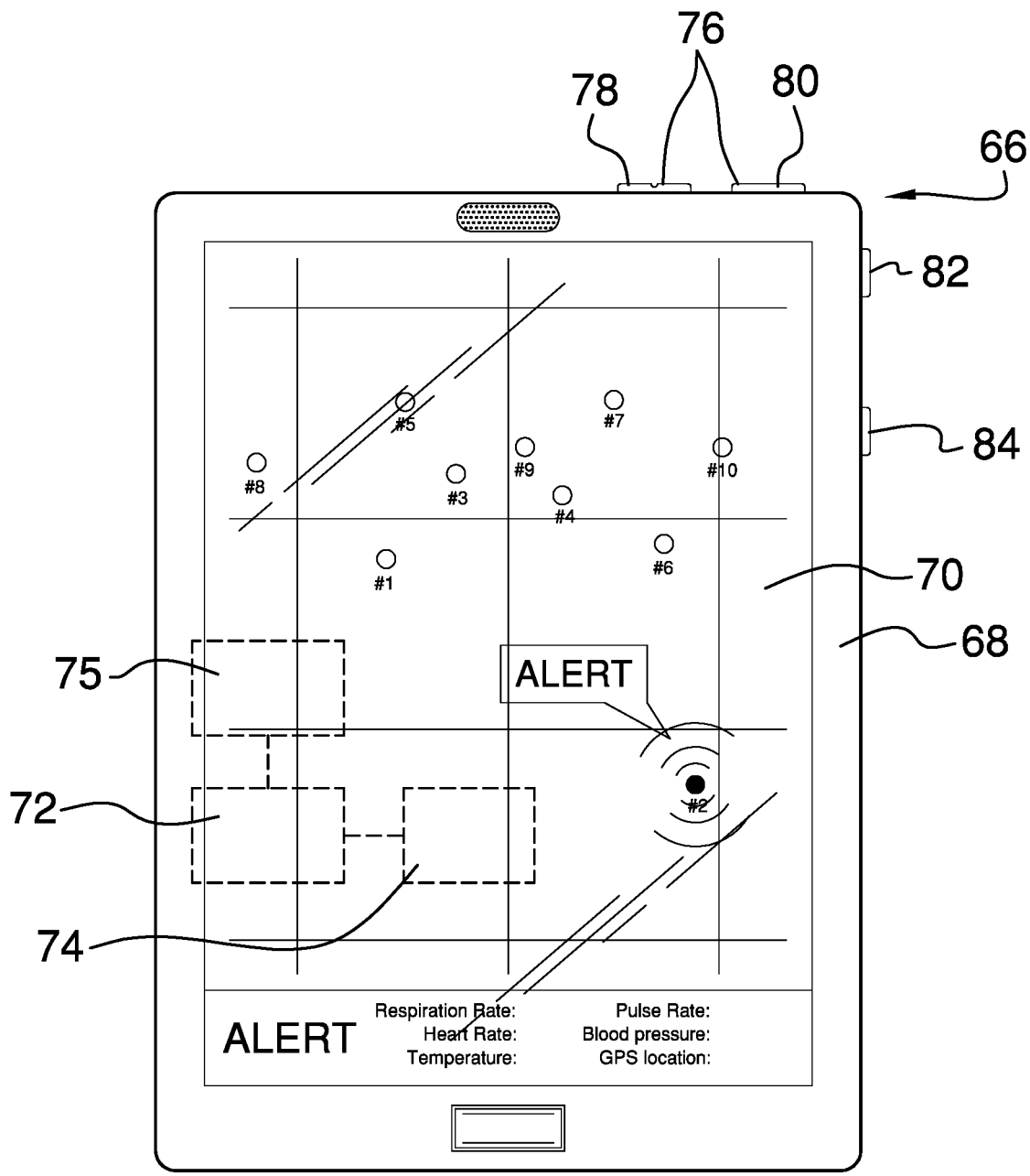
FIG. 5 is a top plan view of an embodiment of the disclosure.

There may alternatively be a main controller 66 shown in FIG. 5. The main controller comprises a controller body 68, a controller display 70 coupled to the controller body 68, and a controller CPU 72 coupled within the controller body 68. The controller CPU 72 is in operational communication with the controller display 70. A controller receiver 74 and a controller battery 75 are coupled within the controller body 68 and are in operational communication with the controller CPU 72. The controller receiver 74 is in operational communication with the transceiver 62 of each swimmer safety monitor apparatus 10. A plurality of control buttons 76 is coupled to the controller body 12 and is in operational communication with the controller CPU 72. The plurality of control buttons 76 may include a controller volume button 78, a controller power button 80, a controller program button 82 to sync with each swimmer safety monitor apparatus 10, and a controller mode button 84 to alternate each swimmer safety monitor apparatus 10 between an adult mode and a child mode.

In use, the swimmer safety monitor apparatus 10 is worn by a swimmer. A supervisor may monitor the swimmer's vitals and location using the personal electronic device 64 or the main controller 66. The panic button 48 is activated by the wearer in case of emergency to send a distress signal to either the personal electronic device 64 or the main controller 66.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

The invention claimed is:

1. A swimmer safety monitor apparatus comprising:
 a transmitter body having a body front side, a body back side, a body top side, a body bottom side, a body left side, and a body right side;
 a strap coupled to the transmitter body, the strap including a first half coupled to the body bottom side and a second half coupled to the body top side, the first half and the second half being selectively engageable to secure the strap and the transmitter body on a user's wrist, the second half of the strap having a flared portion medially positioned between opposed ends of the second half, the second half having an obround strap aperture extending through the second half of the strap within the flared portion such that the strap aperture is positioned to receive a distal end of the first half of the strap relative to the transmitter body whereby the distal end is configured to be positioned between the second half of the strap and the user's wrist;
 a transmitter display coupled to the transmitter body, the transmitter display being coupled to the body front side;
 a CPU coupled within the transmitter body, the CPU being in operational communication with the transmitter display;
 a battery coupled within the transmitter body, the battery being in operational communication with the CPU;
 a power button coupled to the transmitter body, the power button being in operational communication with the CPU;
 a panic button coupled to the transmitter body, the panic button being in operational communication with the CPU;
 a biometric sensor coupled to the transmitter body, the biometric sensor being coupled to the body back side and being in operational communication with the CPU; and
 a transceiver coupled within the transmitter body, the transceiver being in operational communication with the CPU, the transceiver being configured to communicate with a personal electronic device to send vitals from the biometric sensor and alerts from the panic button.

2. The swimmer safety monitor apparatus of claim 1 further comprising a GPS chip coupled within the transmitter body, the GPS chip being in operational communication with the CPU.

3. The swimmer safety monitor apparatus of claim 1 further comprising the biometric sensor comprising a pair of rectangular sensor pads.

4. The swimmer safety monitor apparatus of claim 1 further comprising the biometric sensor reading the wearer's respiration rate, heart rate, body temperature, and blood pressure.

5. The swimmer safety monitor apparatus of claim 1 further comprising the battery being chargeable with an induction charger.

6. The swimmer safety monitor apparatus of claim 1 further comprising the battery having a charge port extending through the body left side.

7. The swimmer safety monitor apparatus of claim 1 further comprising the body top side, the body bottom side, the body left side, and the body right side being rounded.

8. The swimmer safety monitor apparatus of claim 1 further comprising the power button having a cylindrical power button housing coupled to the body right side; the panic button having a cylindrical panic button housing coupled to the body right side.

9. The swimmer safety monitor apparatus of claim 1 further comprising the transmitter display occupying the entirety of the body front side.

10. The swimmer safety monitor apparatus of claim 1 further comprising the first half of the strap having a plurality of adjustment apertures and the second half of the strap having a buckle, the buckle being selectively engageable with the plurality of adjustment apertures.

11. A swimmer safety monitor apparatus comprising:
a transmitter body having a body front side, a body back side, a body top side, a body bottom side, a body left side, and a body right side, the body top side, the body bottom side, the body left side, and the body right side being rounded;
a strap coupled to the transmitter body, the strap including a first half coupled to the body bottom side and a second half coupled to the body top side, the first half and the second half being selectively engageable to secure the strap and the transmitter body on a user's wrist, the first half of the strap having a plurality of adjustment apertures and the second half of the strap having a buckle, the buckle being selectively engageable with the plurality of adjustment apertures, the second half of the strap having a flared portion medially positioned between opposed ends of the second half, the second half having an obround strap aperture extending through the second half of the strap within the flared portion such that the strap aperture is positioned to receive a distal end of the first half of the strap relative to the transmitter body whereby the distal end is configured to be positioned between the second half of the strap and the user's wrist;
a transmitter display coupled to the transmitter body, the transmitter display being coupled to the body front side and occupying the entirety of the body front side;
a CPU coupled within the transmitter body, the CPU being in operational communication with the transmitter display;
a battery coupled within the transmitter body, the battery being in operational communication with the CPU, the battery having a charge port extending through the body left side;
a power button coupled to the transmitter body, the power button being in operational communication with the CPU, the power button having a cylindrical power button housing coupled to the body right side;
a panic button coupled to the transmitter body, the panic button being in operational communication with the CPU, the panic button having a cylindrical panic button housing coupled to the body right side;
a GPS chip coupled within the transmitter body, the GPS chip being in operational communication with the CPU;
a biometric sensor coupled to the transmitter body, the biometric sensor being coupled to the body back side and being in operational communication with the CPU, the biometric sensor comprising a pair of rectangular sensor pads reading the wearer's respiration rate, heart rate, body temperature, and blood pressure; and
a transceiver coupled within the transmitter body, the transceiver being in operational communication with the CPU, the transceiver being configured to communicate with a personal electronic device to send vitals from the biometric sensor and alerts from the panic button.

12. A swimmer safety monitor apparatus and controller system comprising:
at least one swimmer safety monitor apparatus each comprising:
a transmitter body having a body front side, a body back side, a body top side, a body bottom side, a body left side, and a body right side, the body top side, the body bottom side, the body left side, and the body right side being rounded;
a strap coupled to the transmitter body, the strap including a first half coupled to the body bottom side and a second half coupled to the body top side, the first half and the second half being selectively engageable to secure the strap and the transmitter body on a user's wrist, the first half of the strap having a plurality of adjustment apertures and the second half of the strap having a buckle, the buckle being selectively engageable with the plurality of adjustment apertures, the second half of the strap having a flared portion medially positioned between opposed ends of the second half, the second half having an obround strap aperture extending through the second half of the strap within the flared portion such that the strap aperture is positioned to receive a distal end of the first half of the strap relative to the transmitter body whereby the distal end is configured to be positioned between the second half of the strap and the user's wrist;
a transmitter display coupled to the transmitter body, the transmitter display being coupled to the body front side and occupying the entirety of the body front side;
a CPU coupled within the transmitter body, the CPU being in operational communication with the transmitter display;
a battery coupled within the transmitter body, the battery being in operational communication with the CPU, the battery having a charge port extending through the body left side;
a power button coupled to the transmitter body, the power button being in operational communication with the CPU, the power button having a cylindrical power button housing coupled to the body right side;
a panic button coupled to the transmitter body, the panic button being in operational communication with the CPU, the panic button having a cylindrical panic button housing coupled to the body right side;
a GPS chip coupled within the transmitter body, the GPS chip being in operational communication with the CPU;

a biometric sensor coupled to the transmitter body, the biometric sensor being coupled to the body back side and being in operational communication with the CPU, the biometric sensor comprising a pair of rectangular sensor pads reading the wearer's respiration rate, heart rate, body temperature, and blood pressure; and a transceiver coupled within the transmitter body, the transceiver being in operational communication with the CPU, the transceiver being configured to communicate with a personal electronic device to send vitals from the biometric sensor and alerts from the panic button; and a main controller, the main controller comprising:

a controller body;

a controller display coupled to the controller body;

a controller CPU coupled within the controller body, the controller CPU being in operational communication with the controller display;

a controller receiver coupled within the controller body, the controller receiver being in operational communication with the controller CPU;

a controller battery coupled within the controller body, the controller battery being in operational communication with the controller CPU; and a plurality of control buttons coupled to the controller body, the plurality of control buttons being in operational communication with the controller CPU.

\* \* \* \* \*